(12) United States Patent
Kohlbrenner et al.

(10) Patent No.: US 8,556,847 B2
(45) Date of Patent: Oct. 15, 2013

(54) SERVICE LIFE TIMER FOR A DEVICE FOR ADMINISTERING A PRODUCT IN DOSES

(75) Inventors: Philippe Kohlbrenner, Kaltacker (CH); Daniel Kuenzli, Langendorf (CH); Juergen Wittmann, Burgdorf (CH); Christoph Meier, Utzenstorf (CH); Peter Stettler, Kirchberg (CH); Martin Wittwer, Bowil (CH)

(73) Assignee: TecPharma Licensing AG, Burgdorf (CH)

( * ) Notice: Subject to any disclaimer, the term of this patent is extended or adjusted under 35 U.S.C. 154(b) by 219 days.

(21) Appl. No.: 12/794,222

(22) Filed: Jun. 4, 2010

(65) Prior Publication Data

US 2010/0238038 A1      Sep. 23, 2010

Related U.S. Application Data

(63) Continuation of application No. 11/316,388, filed on Dec. 22, 2005, now Pat. No. 7,749,186.

(30) Foreign Application Priority Data

Dec. 31, 2004   (DE) .................. 10 2004 063 650

(51) Int. Cl.
*A61M 31/00* (2006.01)
(52) U.S. Cl.
USPC ............................................ 604/67; 604/500
(58) Field of Classification Search
USPC ............ 604/65–68, 187, 208, 211, 218, 224, 604/228, 234, 240, 500
See application file for complete search history.

(56) References Cited

U.S. PATENT DOCUMENTS

| | | | | |
|---|---|---|---|---|
| 4,828,551 A * | 5/1989 | Gertler et al. | | 604/208 |
| 4,950,246 A | 8/1990 | Muller | | |
| 5,728,074 A | 3/1998 | Castellano et al. | | |
| 5,993,412 A | 11/1999 | Deily et al. | | |
| 6,340,357 B1 * | 1/2002 | Poulsen et al. | | 604/208 |
| 7,635,348 B2 * | 12/2009 | Raven et al. | | 604/111 |
| 2002/0107501 A1 * | 8/2002 | Smith et al. | | 604/500 |
| 2004/0049161 A1 * | 3/2004 | Shearn | | 604/224 |
| 2004/0189258 A1 * | 9/2004 | Lehmann et al. | | 320/132 |
| 2005/0267439 A1 * | 12/2005 | Harr et al. | | 604/500 |

FOREIGN PATENT DOCUMENTS

| | | |
|---|---|---|
| EP | 0 554 996 | 8/1993 |
| EP | 0 285 403 | 10/1998 |
| EP | 0 897 728 | 2/1999 |

* cited by examiner

*Primary Examiner* — Victoria P Shumate
(74) *Attorney, Agent, or Firm* — Dorsey & Whitney LLP; David E. Bruhn, Esq.

(57) ABSTRACT

An injection device including at least one sensor for detecting an operating process of the injection device, an electronic circuit connected to the sensor for establishing the beginning and elapsed time of a service life, based on one or more sensor signals, and an output device connected to the circuit for providing a signal indicating the end of the service life. The invention encompasses a method for determining a service life of an injection device, wherein the beginning of the service life is established by one or more sensors for detecting an operating process of the device, a signal is generated which signals the end of the service life, and at least one of an optical, acoustic or tactile output device is associated with the injection device for providing a signal which indicates the end of the service life.

5 Claims, 8 Drawing Sheets

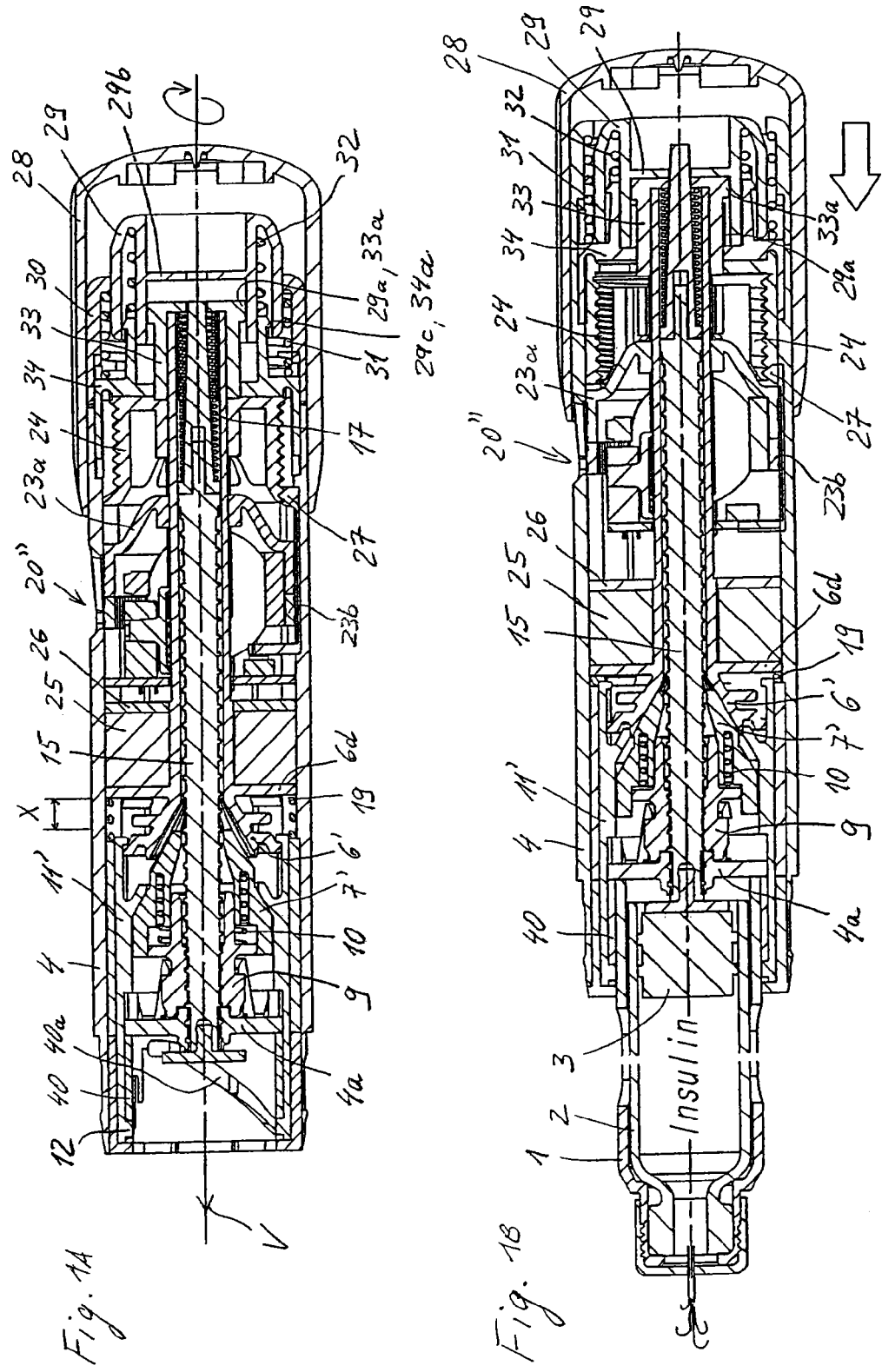

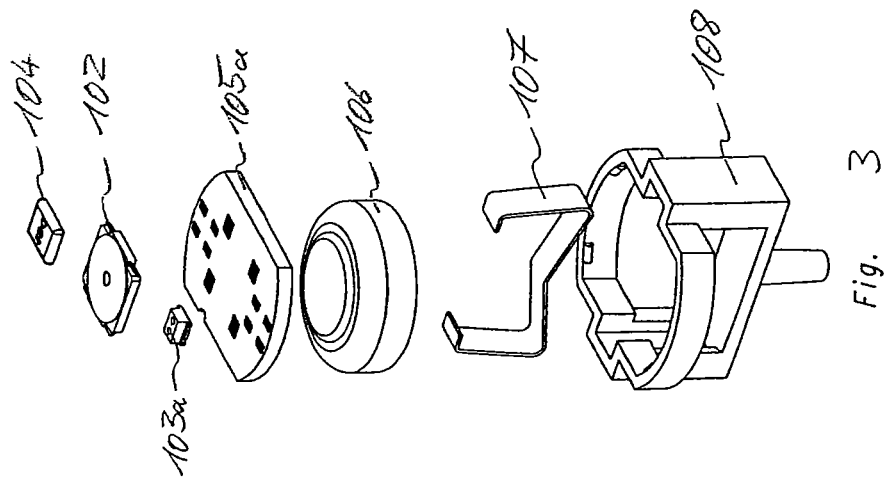
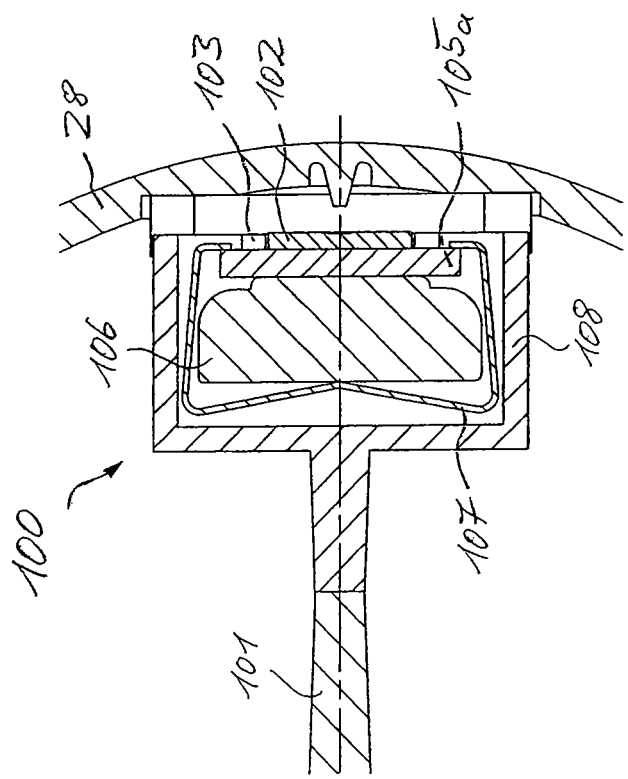

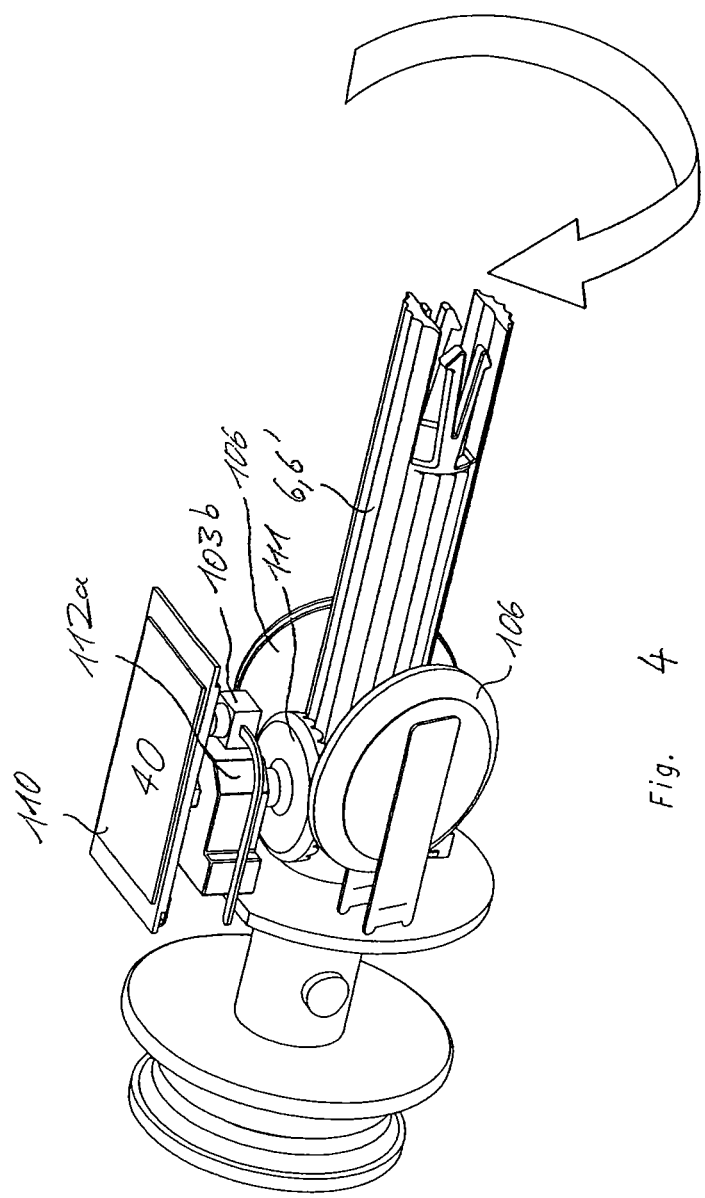

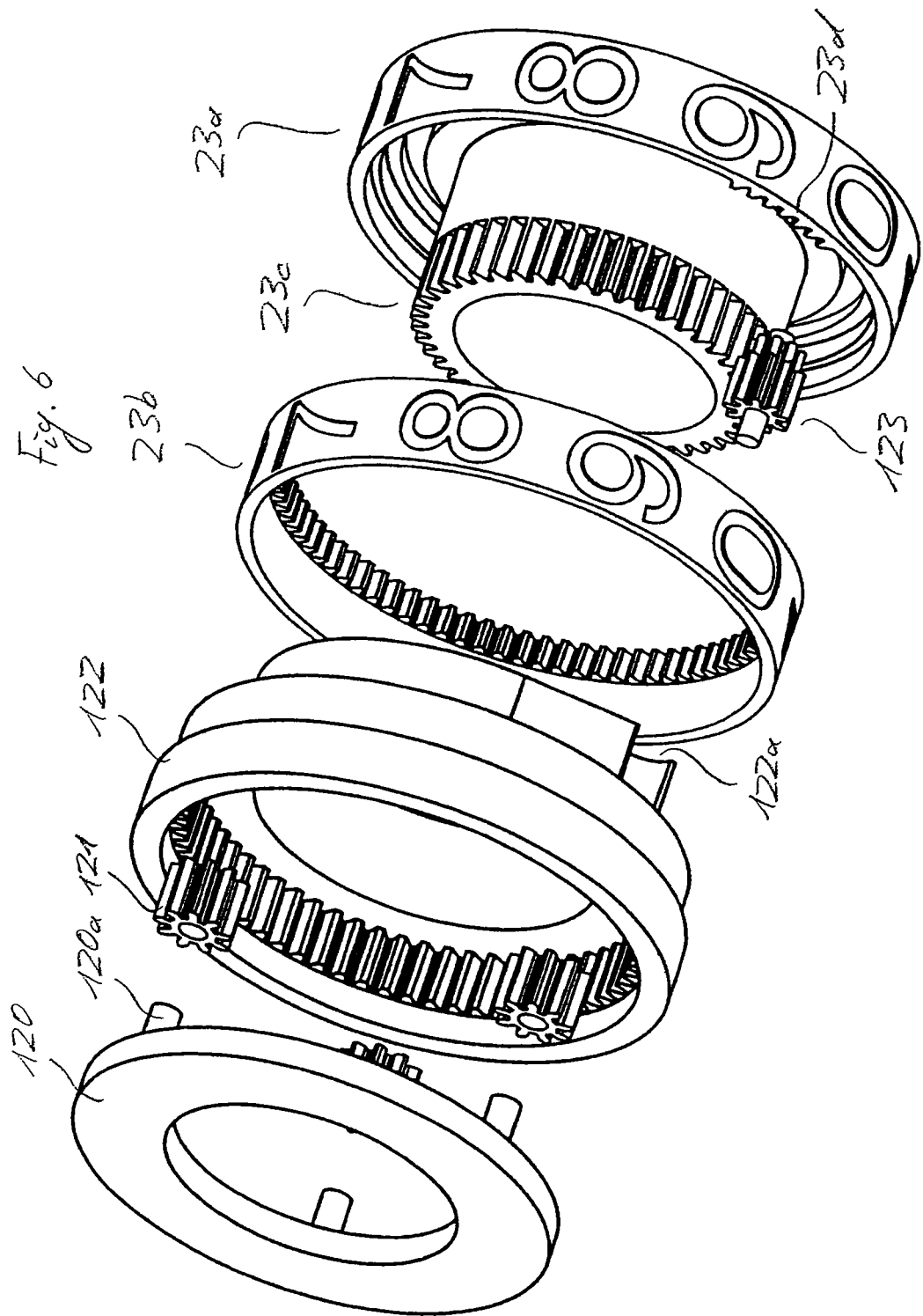

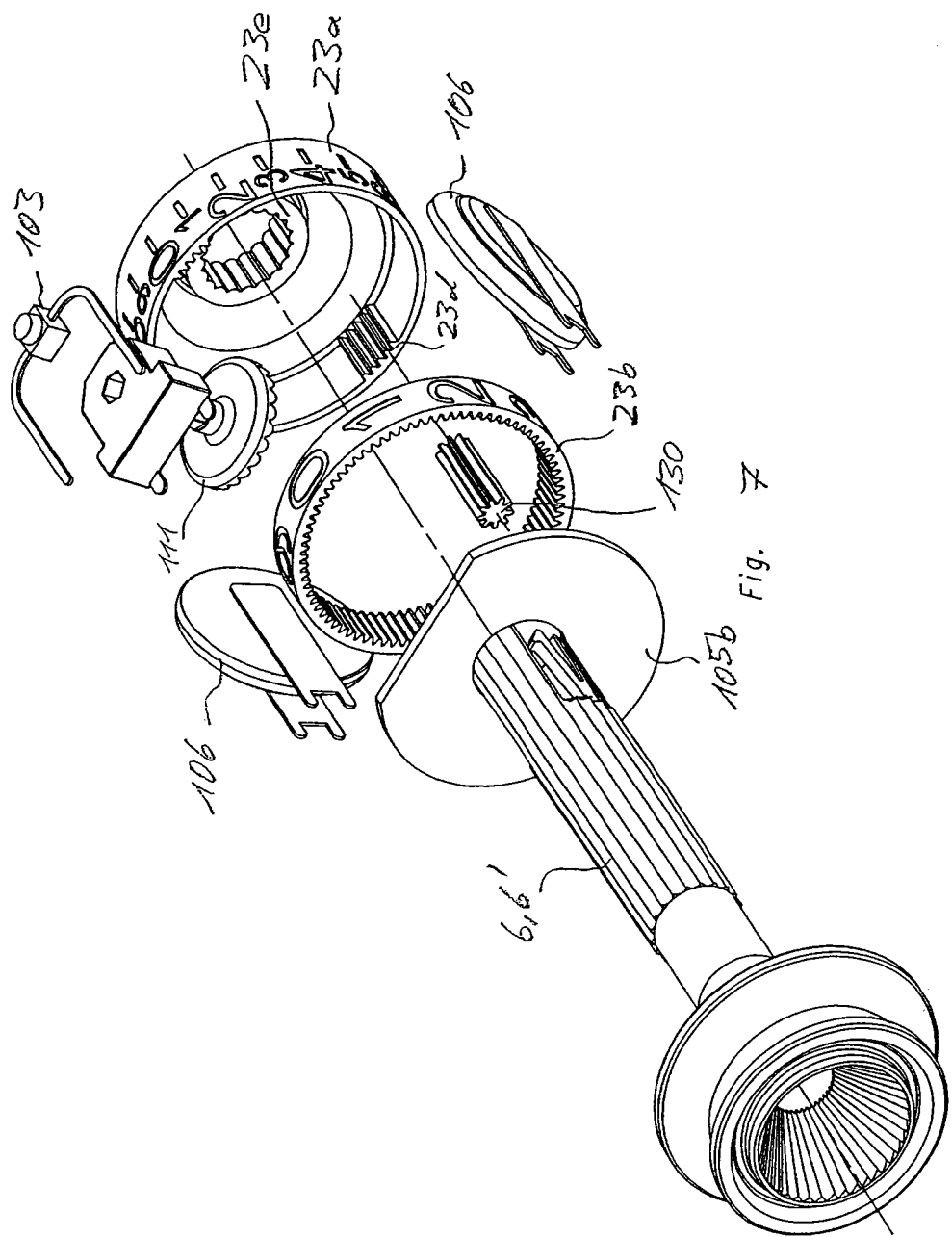

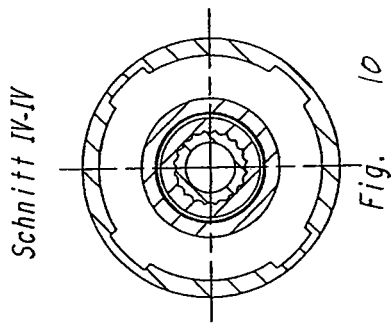
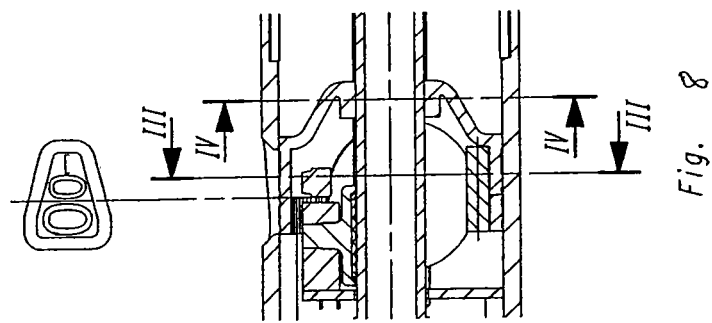
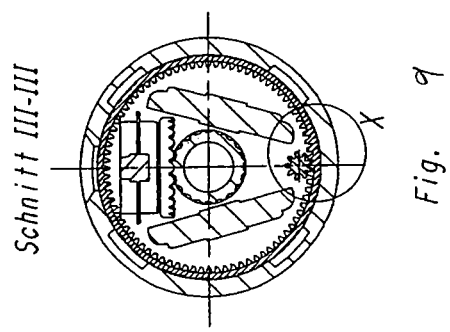
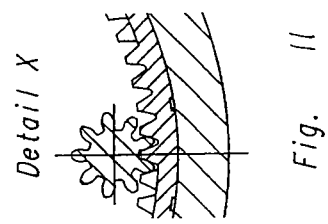

SERVICE LIFE TIMER FOR A DEVICE FOR ADMINISTERING A PRODUCT IN DOSES

CROSS-REFERENCE TO RELATED APPLICATION

This application is a divisional of U.S. Ser. No. 11/316,388, filed Dec. 22, 2005, now U.S. Pat. No. 7,749,186, issued Jul. 6, 2010, which claims the benefit of German Patent Application No. DE 10 2004 063 650.8, filed on Dec. 31, 2004, the entire contents of both of which are incorporated herein by reference.

BACKGROUND

The present invention relates to devices for delivering substances and methods of making and using them. More particularly, it relates to medical devices for administering or delivering a product in doses, such as injection apparatus, syringes, injection pens, etc., using which a dosed amount of a fluid product, such as insulin, growth hormones or osteoporosis preparations, etc., can be self-administered by a user.

The functional elements of an electronic or mechanical real-time display and of an electronic life timer or device service life timer, as described below, may be used together with an injection pen as described in a US patent application entitled "Injection or Infusion Apparatus Comprising a Service Life Timer" filed on the same day as the present application and owned by the owner of the present application. The elements and functional sub-assemblies of injection apparatus, as described in that patent application, are incorporated into this application by reference, wherein an injection pen in accordance with the present invention may incorporate an embodiment of a dosage display described in the referenced patent application, and/or with regard to sensors, electronics or display elements as described herein.

In injection devices, including pen-type devices, components such as springs or components which are often moved can wear, change or deteriorate due to the strains occurring during use and due to mechanical stresses, and also due to aging processes, such that the correct mode of operation and functional capability of the pen is compromised.

If a user sets a dosage or an amount of a substance to be dispensed by the injection device by displacing the substance from an ampoule inserted in the injection device, then it is advantageous for the user if the dosage currently can be set and/or displayed on a display of the injection device. In known injection apparatus, the dosage set is displayed during and after setting the dosage, and the user can initiate the injection process by pressing a triggering button, wherein the dosage displayed rotates or runs back or is reset from the dosage set to zero after the injection process has been performed.

SUMMARY

It is one object of the present invention to provide a device and a method for monitoring, assessing and/or determining the service life of an injection pen and the end of the service life can be displayed.

It is another object of the present invention to propose a device and a method which provide the user of an injection device with additional information for performing an injection process which has been interrupted.

In one embodiment, the present invention comprises an injection device including at least one sensor for detecting an operating process of the injection device, an electronic circuit connected to the sensor for establishing the beginning and elapsed time of a service life, based on one or more sensor signals, and an output device connected to the circuit for providing a signal indicating the end of the service life. The invention encompasses a method for determining and/or monitoring a service life of an injection device, wherein the beginning of the service life is established by one or more sensors for detecting an operating process of the device, a signal is generated which signals the end of the service life, and at least one of an optical, acoustic or tactile output device is associated with the injection device for providing a signal which indicates the end of the service life.

In accordance with one embodiment of the present invention, an injection device comprises at least one sensor in order to detect at least one dose setting or other operating process of the injection device. A mechanical switch or pressure switch can, for example, be provided as a sensor on the injection device in the region of a dosing member, an injection button or other suitable location, to detect, for example, when the injection device is activated for the first time or when an ampoule is inserted. It is also possible for a sensor or switching element to be provided at another point on the injection device, such as in the region of a reservoir into which an ampoule is inserted, or coupled via a connecting member to a component of the injection device, to detect when an ampoule is inserted. It is also possible to provide an encoder or rotational sensor as the sensor, which may be coupled to a dosing member, a piston rod or threaded rod of the injection device by means of a suitable engagement, for example, via a spur wheel, a toothed ring or a toothed wheel, mounted approximately parallel to the central axis of the injection device, to detect a setting or delivery process of the injection device.

In accordance with an embodiment of the present invention, any sensor can in principle be used which is suitable for detecting when the injection device is activated or operated for the first time, or using which an operating process or activating process of the injection device, for example for setting a dosage to be dispensed, for drawing up the injection device, for preparing an injection process, for performing an injection process, for delivering a set dosage or for changing an ampoule, can be detected. By means of one or more such sensors for qualitatively or quantitatively detecting operating processes, operational or state parameters, it is possible to detect when an injection device has been activated or operated for the first time, to start a timer provided in the injection device, which, after a fixed time period, for example three years, predetermined by the manufacturer, outputs a signal in order to indicate that the service life of the injection device—for which the manufacturer of the injection device guarantees the correct mode of operation of the injection device—has elapsed.

Such a timer may be based on mechanical or chemical principles, wherein for example a chemical substance which changes its colour after a predetermined time period can be provided such that a user can recognise from the colour whether the injection device has exceeded the recommended or indicated service life.

In such embodiments, a timer is provided or enabled by an electronic circuit connected to at least one of the sensors described above and receives a start signal from one or more of these sensors, for example when the injection device is activated for the first time or when a full ampoule is inserted. Once a time period predetermined or set by the manufacturer, user or calculated by the circuit has elapsed, taking into account stresses on the injection device, the circuit outputs a signal to a display or a lamp, to indicate to a user that the end of the service life of the injection device has been reached.

When, once the timer has elapsed, it is established that the service life of the injection device has elapsed, then it is possible to generate one of an optical, acoustic and/or tangible or tactile signal in order to indicate to the user that injection device should no longer be used for safety reasons. However, the injection device can in principle continue to be used, wherein for example a corresponding warning signal, such as for example the illumination or blinking of a red LED or OLED, can be generated in the process of use. Alternatively, it is also possible for a stop signal outputted by an electrical or mechanical circuit, to an actuator such as an electromotor, a magnetic switch or a locking element, to be outputted once the end of the service life of the injection device has been established, such that the actuator places the injection device in a state in which it can no longer be used and in which no further dosages can be dispensed, i.e., for example blocking or locking a rotatable setting element, permanently decoupling functional sub-assemblies of the injection device which have to be coupled to each other during a setting or dispensing process, or preventing an injection button from being activated by creating a permanent, fixed connection between the injection button and the injection device.

In some embodiments a data memory can also be provided in the injection device, together with a timer, in which data can be stored relating to the service life, setting or operating processes performed on the injection device. Such data may relate to the time when the injection device was operated for the first time, the number and/or time of the dosage setting processes and/or delivery processes, and/or the number and/or times of ampoule changes. A processor or controller provided in the injection device can compare the data on the use of the injection device stored in the memory with limit values for the maximum permissible use of the injection device, fixedly predetermined or set by the manufacturer, in order to output a signal when the maximum permissible number of ampoule changes or delivery processes has been reached or exceeded, in order to generate a warning signal as described above, which indicates to the user that the maximum number of ampoule changes or delivery processes has been reached or exceeded. If operating or operational parameters of the injection device are used to ascertain the end of the service life of the injection device, then the service life time period can vary depending on how the injection device is used by the user.

It is also possible for the end of the service life to be ascertained by taking into account various parameters, such that the service life of an injection pen which is not used ends after a predetermined time period, for example three years, wherein for each operating process of the injection device detected by one or more sensors, such as an ampoule change or a delivery process, a predetermined time period is deducted from the maximum service life, such that a pen which is used often after it has been operated for the first time generates a signal indicating that the end of the service life has been reached earlier than a pen which is only rarely used.

If the life timer is controlled via the number of ampoule changes detected by a sensor, then a so-called system check can additionally be performed. If the ampoule is full, then a switch of the life timer is activated via the threaded rod and a connecting piece, which briefly illuminates the LED green.

In some preferred embodiments the display for the user that the end of the service life has been reached is an optical display and can comprise the electronic, mechanical or electro-mechanical display provided for displaying a dosage set, such as an LCD display and—additionally or alternatively—one, two or more counting rings or counting discs, on which a signal is directly generated or set which indicates the end of the service life to a user. A lamp, such as an LED, OLED, other suitable light source, can also be provided which is illuminated or blinks for the first time or changes the colour when the end of the service life has been reached.

Thus, for example, a multi-coloured OLED or LED or a red LED can be provided on or in the injection device, provided next to a green LED for illuminating a setting display, in order to indicate to a user, who is usually looking at the setting display, by a red light that the injection device should no longer be used. One or more OLEDs or LEDs can be provided behind an LCD display or within coaxially arranged and at least partially or completely transparent counting rings or counting discs for displaying the dosage, such that the red light of the LED or OLED shines through the transparent counting rings or counting discs. Another lamp can be provided in the vicinity of or next to a lamp for displaying the end of the service life, which is illuminated in a different colour and/or emits light of a different intensity as compared to the service life displaying lamp. For example, a green LED may be illuminated behind an electronic or mechanical display when a sensor establishes that a user is activating a setting or activating element of the injection device, whereby the user can read the dosage set, even in darkness or poor lighting conditions. Once the end of the service life has been ascertained, this lamp can be permanently switched off or switched to emitting different-coloured light, such that the service life ending display or lamp blinks or is illuminated permanently or once it is been detected that the user is operating or setting the injection device. Thus, a user does not see the green light which is usually perceives during a setting process, but rather can recognise from the red light and/or a blinking light then generated that the end of the service life of the injection device has been reached and that it consequently should no longer be used, even if it is in principle possible to continue to use the injection device.

In order to supply the sensors, circuits, controllers, processors, memories or displays provided in the injection device with energy a suitable power source may be provided, e.g., a battery, a button cell or a power pack which can be charged up, wherein the optical display elements described above can also be used to indicate to a user that the power pack should be charged up again.

The present invention also relates to a method for determining assessing and/or monitoring the service life or service life interval of an injection device, wherein a beginning of the service life is ascertained by a sensor by detecting an operating process by a user, and wherein the sensor generates a signal which defines a time at which the service life begins. Once it has been established that the predetermined service life, or a recalculated service life shortened by operating processes or other parameter, has elapsed, an optical and/or acoustic signal is generated immediately or at the next detected operating process, which can indicate the end of the service life to a user.

The present invention also relates to a computer program or an algorithm for performing, controlling or enabling, using any task or function can be performed, i.e., calculating a service life by taking into account the operating processes which shorten the service life, such as injection processes or ampoule changes.

In accordance with another aspect, the present invention relates to an injection device comprising a real-time display for continuously displaying a dosage set for dispensing by the injection device and still to be dispensed. An injection device in accordance with the present invention, in which a substance to be dispensed is contained or can be inserted in an ampoule, comprises a setting element such as a dosing button or dosing member which can set or define a dosage provided for dispensing or injecting, by being moved, rotated or shifted, such as drawn out. At least one sensor is also provided which is directly or indirectly connected to the setting element or a setting or dispensing mechanism of the injection device, for example coupled via toothed wheels, in order to detect the amount of a dosage of a substance available for dispensing from the injection device. An evaluation unit such as an electrical circuit or a processor connected to the at least one sensor can ascertain what dosage is currently set or what dosage is still available for dispensing by the injection device on the basis of the setting, directly on the basis of the signals from the at least one sensor, i.e. directly from the signals, or from the chronological profile of the signals, i.e. by taking into account previous signals of the at least one sensor. In accordance with the present invention, the evaluation unit also ascertains the amount of the dosage set and still available for dispensing or delivery but not yet delivered, while the substance contained in the injection device is being dispensed. A display connected to the evaluation unit can display the dosage set by a user, for example as a numerical value, such that the dosage set can be read on an LCD or by means of mechanically coupled counting wheels or rings. In accordance with the invention, a regressing dosage or number can be displayed on the display while a substance is being delivered.

A mechanical or electronic display of the injection device can thus display the current value of the amount of substance already dispensed or the dosage not yet delivered or the state of the mechanism, as a real-time display.

If, for example, a delivery process is interrupted, then a user can establish what amount of a substance has injected, or what dosage must still be injected.

In some embodiments, an electronics unit of the injection device is preferably constructed in modules, i.e., the injection device is designed such that it is possible to combine the electronics unit with a mechanical or electronic display inserted or snapped on during assembly, wherein different casing shells can also subsequently be used. It is thus not necessary for the injection device to be modified in order to integrate either a mechanical or electronic display into the injection device. The electronics unit can preferably be provided as a sub-assembly for directly assembling in the injection device, which enables plastic parts and their assembly steps to be eliminated.

Using a real-time display in accordance with the invention, it is thus possible to display both setting or correcting a dosage, delivering, and—if necessary—correcting a set dosage, during a delivery process.

By continuously measuring or calculating the amount of the substance dispensed during a delivery process and/or of the substance still available for delivery and amounting to a maximum value of the dosage set, it is possible for an evaluation unit or circuit contained in the injection device or a user reading the display to verify whether the delivery process is proceeding correctly, is already complete, or still has to be performed further. A user is thus provided in real-time, i.e. immediately, with the information which enables him/her to assess what operational state the injection device is in, i.e., whether a partial amount of a set dosage set has already been dispensed, or what amount of the dosage has already been dispensed or is still to be delivered. A user can thus also discontinue the injection in a controlled and defined way, and continue it at a later time.

In some embodiments, a sensor for detecting the dosage still to be dispensed is preferably coupled or connected to a setting element or a delivery mechanism of the injection mechanism, such as for example a piston rod or a coupler element as described in the aforementioned patent application owned by the applicant. The sensor preferably continuously detects the current operational state of the injection device or information and parameter, such as a rotational angle or the number of revolutions of a unit provided in the injection device for setting or delivering a dosage, such as a coupler, piston rod or toothed rod. The sensor can, for example, be a rotational switch or encoder which preferably does not comprise a stopper. One suitable, exemplary encoder is manufactured for example by Alps Electric Co., Ltd. of Tokyo, Japan. An encoder can detect a rotational movement of a setting element or dosing member directly, or the rotation of a coupler sleeve or of a spur wheel or toothed wheel in engagement with the coupler sleeve, wherein the signal detected by the encoder can be processed by electronics contained in the injection device and forwarded to an LCD for the user to read. Such an encoder can also be used as a sensor for a life timer as described above for detecting the beginning of the service life or of a setting or delivery process.

The display used to display the dosage still available for delivery can be an LCD display provided in an electronics sub-assembly or in an "E module" of the injection device and can be illuminated or transilluminated by a lamp or LED as described above. A mechanical display can also be provided, for example in the form of one, two or more counting rings such as are described in EP 0 554 996 B1 or EP 0 897 728 A1, the teachings of which relating to the mechanical configuration and coupling of units counting rings and tens counting rings is incorporated by reference into this application.

In some embodiments a real-time display of the injection device can be provided with mechanical elements as a coaxial display of two or more adjacent counting rings which are inscribed in the circumferential direction with the digits "0" to "9" as is known from tachometers in motorised vehicles or counters in cassette machines. Such a display, comprising coaxially adjacent counting rings and/or counting discs, can be provided coaxially on the injection device, such as in the rear region of the injection device in the vicinity of a setting button or dosing member, and coupled to such a setting button or dosing member, such that whenever a dosing member or dosing wheel is moved, the mechanical display rotates with it, when dosing up, correcting a dosage or delivering. In accordance with the present invention, the mechanical display is coupled to a setting and/or delivery or dispensing mechanism of the injection device such that even during the delivery process, the mechanical display displays the amount of the dosage still to be delivered, i.e., the mechanical display counts backwards while the substance contained in the injection device is delivered.

In some embodiments, the mechanical counter is preferably provided with a planetary drive for rotating the counting wheels, wherein a drive disc which is coupled to a setting element such as a dosing member or to an element of the delivery mechanism such as a toothed rod or piston rod or to a coupler or coupler sleeve drives one, two, three or more planetary wheels which are coupled to the drive disc or mounted on the drive disc. These planetary wheels engage with a toothing provided on the outer side of a units counting ring and so drive the units counting ring. On the inner or outer side of the units counting ring, a toothing (on teeth) is provided in the circumferential direction, only within a range of for example 36 degrees preferably corresponding for instance to one units counting increment. Thus, after each full revolution, the units counting ring can drive a coupling or transferring toothed wheel engaged with said toothing, which after each full revolution of the units counting ring drives a tens counting ring provided coaxially to the units counting ring, such that the tens counting ring is rotated further by a predetermined value of 36 degrees, to rotate a digit provided on the tens counting ring forwards or backwards to the position of an adjacent digit. A hollow wheel can serve as a bearer for the units and tens counting rings and comprises a toothing on its inner side, with which the planetary wheels driving the units counting ring engage. The coupling toothed wheel can also be mounted in the hollow wheel. The hollow wheel is preferably mounted in the casing of the injection device such that it is secured against rotating, or is integrated into it.

By defining measurements or parameters of the toothing, the transfer ratio of the drive disc onto the units counting ring can be defined, such that it is possible for the units counting ring to pass through 2.4 revolutions for one revolution of the drive disc, though other transfer ratios can also be realised by correspondingly changing the toothing distances or variations in diameter of the mutually engaging toothed wheels or encircling rows of teeth.

The counting rings can be produced from a non-transparent material or as described above from a transparent material, such that the light from one or more lamps or LEDs arranged within the counting rings can pass out through the counting rings, in order to enable a user to read a dosage set, even in darkness.

The present invention also relates to a method for displaying a dosage to be dispensed by an injection device after a setting process, wherein a dosage set is detected and displayed and the amount of the dosage still to be delivered is continuously measured or ascertained and displayed during a delivery and dispensing process, such that a regressing display can be realised during a delivery process.

In one embodiment, the display is preferably reset to "0" when the ampoule is changed or when the dosage set has been delivered or when it is established—for example by a sensor and/or components of the injection device that abut or contact each other or a stop been completely performed—that a further dosage can no longer be delivered without another setting process. A display can thus be automatically zeroed after each delivery and/or ampoule change, in order to ensure that the display or the electronics of the injection device does not lose any counting increments and is available again for a new setting process starting from a defined initial state. A mechanical display can be automatically rotated back to "0" by a drive member as shown in FIGS. 1A to 1C, i.e., for example a torsion spring or spiral spring, when the pen is screwed open to change the ampoule.

In some embodiments, an electronic display of the injection device and/or an illumination of an electronic or mechanical display, such as for example an LED, can be switched on when a sensor establishes that the injection device is being activated or moved, and can be switched off again when a predetermined time period of, for example, 30 seconds has passed, when it is established that the injection device has not been activated within a predetermined time period, or when it is established that a delivery process is complete.

BRIEF DESCRIPTION OF THE DRAWINGS

FIG. 1, including FIGS. 1A to 1C, is a cross-sectional view of an embodiment of an injection device as described in the co-owned aforementioned patent application filed on the same date as the present application;

FIG. 2 depicts a sensor for an electronic life timer in the dosing button, in cross-section;

FIG. 3 depicts the sensor of FIG. 2 in an exploded view;

FIG. 4 depicts an embodiment of an electronic real-time display, comprising a spur wheel for coupling the sensor to the setting and delivery mechanism;

FIG. 5, including

FIG. 6 depicts a coaxial real-time display driven by a planetary gear;

FIG. 7 depicts a mechanical coaxial real-time display, comprising a life timer;

FIG. 8 is a detailed cross-sectional view of a portion of the injection device shown in FIG. 1;

FIG. 9 is a sectional view of the detail shown in FIG. 8;

FIG. 10 is a sectional view of the detail shown in FIG. 8; and

FIG. 11 is a detailed view of the region indicated by X in FIG. 9.

DETAILED DESCRIPTION OF THE DRAWINGS

Figure 1C:
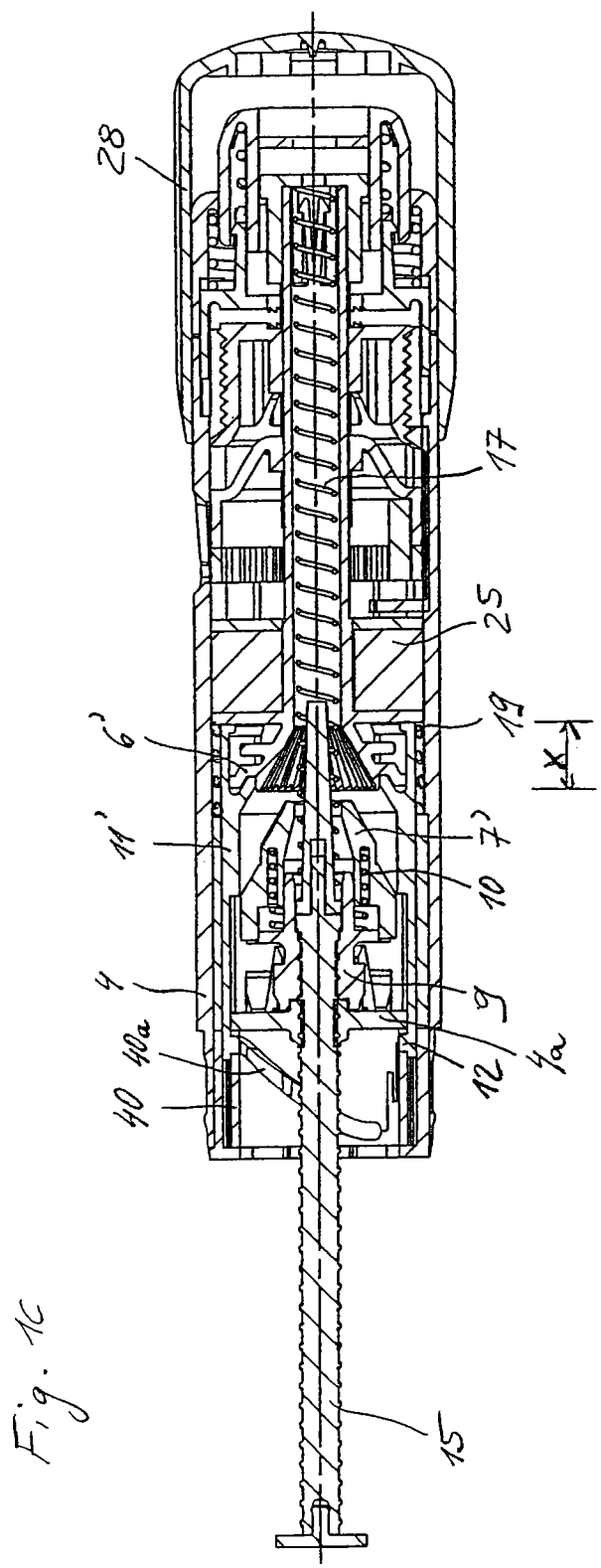

FIGS. 1A to 1C show cross-sections of an embodiment of an injection device in which a life timer and/or an electronic or mechanical real-time display may be integrated.

With regard to fastening, mounting, attaching or connecting the components of devices of the present invention, unless specifically described as otherwise, conventional fasteners such as screws, rivets, toggles, pins and the like may be used. Other fastening or attachment means appropriate for connecting components include friction fitting, adhesives, welding and soldering, the latter particularly with regard to electrical or processing components or systems of the devices. Any suitable electronic, electrical, communication, computer or processing components may be used, including any suitable electrical components and circuitry, display components, wires, wireless components, sensors, chips, boards, microprocessing or control system components, software, firmware, hardware, etc.

FIGS. 1A to 1C show an embodiment of an injection apparatus in accordance with a US patent application entitled "Injection or Infusion Apparatus Comprising a Service Life Timer" filed on the same day as the present application and owned by the owner of the present application. When using the depicted device for administering, the drive force for delivering the product is not applied manually, but rather by a drive member 25 formed as a drive spring. The drive member 25 is a spiral spring acting as a torsion spring, comprising spring windings which encircle the threaded axis of the threaded engagement between the coupler output member 9 and the piston rod 15. The spring windings are arranged one over the other, radially with respect to the threaded axis; they exhibit a zero pitch with respect to the threaded axis. An inner end of the spring windings is fastened to the coupler input member 6', and an outer end is fastened to a fastening structure 26 which is connected to the casing part 4 such that it can be moved in the direction of the coupler movement X but is secured against rotating. On the other hand, the fastening structure 26 is connected to the coupler input member 6' such that it cannot be moved in and counter to the direction of the coupler movement X. The coupler input member 6' can be rotated about the threaded axis relative to the fastening structure 26.

The functionality of the coupler corresponds to that of the second exemplary embodiment of the parallel patent application, such that the same reference signs are used for the coupler members and the decoupling member 11'. Unlike the coupler of the second exemplary embodiment, however, the coupler sleeve 8' therein has been omitted. The coupler intermediate member 7' is directly in an engagement with the coupler output member 9 which transfers the rotational drive movement of the coupler input member 6' onto the coupler output member 9.

In the embodiment shown in FIGS. 1A to 1C, the holding means is formed in a third variant. It includes a restoring element 19, as well as the coupler receptacle which again forms the linear guide 4a for the piston rod 15, and a supporting structure 6d which is connected to the coupler input member 6' such that it cannot be moved at least in and counter to the direction of the coupler movement X; in the exemplary embodiment, the coupler input member 6' and the supporting structure 6d are formed integrally. The drive member 25 is axially enclosed by the supporting structures 6d and 26. The restoring element 19 is supported on the casing part 4 via the coupler receptacle in the direction of the coupler movement and on the supporting structure 6d counter to the direction of the coupler movement X. The restoring element 19 exerts an elastic restoring force, acting counter to the coupler movement X, on the coupler input member 6'. It again acts as a pressure spring.

The equalising spring 17, tensed between the piston rod 15 and the connecting part 33, supports the restoring element 19. The equalising spring 17 could in principle replace the restoring element 19 for retracting the coupler members 6', 7' and 9. Preferably, however, it is weak enough that, at least once it has been partially relaxed, it can no longer hold the coupler members in the holding position, and thus can no longer hold the coupler in the decoupled state, with sufficient certainty.

20" indicates a dosage display which is coupled to the coupler input member 6' via a display coupling member or units counting ring 23a and mechanically coupled to a tens counting ring 23b, as shown in FIG. 6 by means of a planetary gear. The operable coupling may be provided as shown in FIGS. 7 to 11, and like the display coupling members 21 and 22 of other embodiments, it is connected to the coupler input member 6' such that it is secured against rotating, or can be coupled to the coupler input member 6'. The display coupling member 23 cannot be moved in and counter to the direction of the coupler movement X relative to the casing part 4. FIG. 1A shows the casing part 4 with the parts of the injection apparatus accommodated in it, in a resting state in which the apparatus can be stored or the product dosage set. In order to prevent the coupler input member 6' from the rotational drive movement, and to hold the drive member 25 in its tensed state, a rotational block or lock is formed between the coupler input member 6' and the casing part 4. In the holding position of the coupler members 6', 7' and 9 shown, the rotational block exists between a first blocking member 24 and a second blocking member 34. The blocking member 24 is connected to the coupler input member 6', such that it is secured against rotating. The blocking member 34 is connected to the casing part 4, such that it is secured against rotating but can be moved in and counter to the direction of the coupler movement X relative to the casing part 4 and the coupler input member 6'. The facing areas of the blocking members 24 and 34, which contact each other in the blocking engagement, form a ratchet which allows a rotational movement of the coupler input member 6' which tenses the drive member 25, and prevents a rotational movement in the opposite direction.

For a second function connected with dosing and delivery, a shell outer area of the blocking member 24 is provided with a thread, the threaded axis of which is coaxial with the threaded axis of the piston rod 15. A stopping member 27 engages with this thread. The stopping member 27 is guided such that it can be linearly moved parallel to the threaded axis of the blocking member 24. In the exemplary embodiment, it can be moved in an axial groove on the inner shell area of the casing part 4. The blocking member 24 forms a rotational stopper for the stopping member 27, which limits the rotational movement of the coupler input member 6' which advances the piston rod 15. It forms another rotational stopper for the stopping member 27, which determines the maximum dosage which can be delivered and set.

A triggering element 28 is provided for triggering the drive member 25. The triggering element 28 can be moved translationally relative to the casing part 4 in the direction of the coupler movement X—in the exemplary embodiment, the advancing direction V and/or the distal direction—and rotationally about the rotational axis of the coupler input member 6', which coincides with the threaded axis of the piston rod 15, and is guided in these two movements by the casing part 4. The translational movement in the distal direction establishes the coupler engagement between the coupler input member 6' and the coupler intermediate member 7' and releases the rotational block between the blocking members 24 and 34, which triggers the drive member 25, i.e., delivery.

In another function, the triggering element 28 forms the dosing member of another exemplary embodiment. Via multiple intermediate members, the rotational movement of the triggering element 28 relative to the casing part 4 sets the product dosage which can be delivered by the next delivery process. From the zero dosage position, which is shown in FIG. 1A and determined by the stopping member 27 abutting the rotational stopper of the blocking member 24 which limits the drive movement of the coupler input member 6', the dosage can be set by rotating the triggering element 28 in the direction of the rotational direction arrow indicated. The rotational dosing movement of the triggering element 28 is transferred onto the coupler input member 6' via an inner part 29, which is connected to the triggering element 28 such that it is secured against rotating and shifting or is formed integrally with it, and a connecting part 33. For transferring, the inner part 29 and the connecting part 33 are in an engagement with each other, such that they are secured against rotating, and the connecting part 33 is connected to the coupler input member 6', such that it is secured against rotating. The connecting part 33 also connected to the coupler input member 6', such that it cannot be moved axially. For securing against rotating, the inner part 29 and the connecting part 33 are provided with an inner toothing (or other suitable meshing, linking or transferring means) 29a and an outer toothing 33a which interlock with each other in the resting state of the apparatus and can be axially shifted with respect to each other.

The triggering element 28 is arranged in the proximal end region of the casing part 4 so as to be user-friendly. Its outer sleeve part surrounds the casing part 4. A base of the triggering element 28 forms a distal end of the injection apparatus. For setting the dosage, the triggering element 28 can be operated as a turning button and is ribbed on its outer shell area for this purpose. For triggering, it can be operated as a push button.

A stopper element 29b projects from the inner part 29 towards a proximal facing area of the connecting part 33. In the resting state of the apparatus, a clear distance remains between the connecting part 33 and the stopper element 29b, which is complementarily just large enough that the rotational block between the inner part 29 and the connecting part 33 is released during the triggering movement of the triggering element 28, before the stopper element 29b terminates the relative movement of the triggering element 28 relative to the connecting part 33 by abutting contact.

The second blocking member 34 is tensed into the blocking engagement with the blocking member 24 by means of a blocking spring 31. For this purpose, the blocking spring 31 is supported in the direction of the coupler movement X on the blocking member 34 and counter to the coupler movement X on a casing part 30 which is fixedly connected to the casing part 4. Another spring 32, arranged between the inner part 29 and the blocking member 34, tenses the triggering element 28 relative to the blocking member 34 into a proximal end position.

In the resting state shown in FIG. 1A, the user sets the dosage by rotating the triggering element 28 in the direction of the rotational arrow. During this rotational dosing movement, the triggering element 28 slaves the connecting part 33 via the rotational block 29a, 33a, which for its part slaves the coupler input member 6' which thus completes the same rotational dosing movement as the triggering element 28. Rotating the coupler input member 6' tenses the drive member 25. In the engagement with the thread of the blocking member 24, the stopping member 27 migrates from the stopper of the thread determining the zero dosage in the direction of the stopper determining the maximum dosage.

If the user has inadvertently set too high a dosage, it can be corrected by rotating the coupler input member 6' back. For correcting the dosage, the triggering element 28 is moved in the proximal direction. In the resting state of the apparatus, the inner part 29 and the blocking member 34 are in a slaving engagement with respect to a movement in the proximal direction. The corresponding slaving means are indicated by 29c and 34a. The slaving means 29c formed by the inner part 29 and the slaving means 34a formed by the blocking member 34 grip behind each other and form a latch for a movement of the triggering element 28 in the proximal direction. By pulling on the triggering element 28, the blocking member 34 is thus also moved in the proximal direction and is thus released from the blocking engagement with the blocking member 24. As soon as the rotational block is released, the user can correct the dosage by means of the translational dosing movement of the triggering element 28 and the still extant rotationally secured engagement between the inner part 29 and the connecting part 33. As soon as the user releases the triggering element 28, it snaps back together with the blocking member 34 due to the effect of the blocking spring 31 in the distal direction and the blocking member 34 thus snaps back into the blocking engagement with the blocking member 24. During the reverse movement, the user expediently continues to hold the triggering element 28 fast, though only to prevent relative rotational movements in the casing part 4. In principle, however, it can also be allowed to snap back.

Once the desired dosage has been set, the apparatus is placed onto the skin at the desired administering location, and the injection needle is injected. For injecting the needle, the user presses the triggering element 28 in the distal direction. A needle protecting sleeve, not shown in the figures, is correspondingly coupled to the triggering element 28. As soon as the injection needle has been placed, the drive member 25 can be triggered and the product delivered by pressing further onto the triggering element 28. In the second phase of the triggering movement of the triggering element 28, which follows the phase for injection, the triggering element 28 and therefore the inner part 29 is pressed further in the distal direction relative to the connecting part 33, against the pressure of the spring 32, such that the rotational block 29a, 33a is released. The triggering element 28 can rotate idly or freely. As soon as the rotational block 29a, 33a has been released, the stopper element 29b passes into abutting contact with the connecting part 33. In the third phase of the triggering movement which then follows, the triggering element 28 presses the connecting part 33 and therefore the coupler input member 6' via the stopper element 29b, in the direction of the coupler movement X; in the exemplary embodiment, in the advancing direction V. Due to the effect of the spring force of the blocking spring 31, the blocking member 34 follows this movement until it abuts against the casing part 4. Before the blocking member 34 reaches the abutting position, the coupler input member 6' passes into the coupler engagement with the coupler intermediate member 7'. The coupler input member 6' presses the coupler intermediate member 7' out of the frictional-lock blocking engagement with the decoupling member 11'. Once the blocking engagement between the conical areas of the two members 7' and 11' has been released and the coupler engagement therefore completely established, the blocking member 34 abuts the casing part 4. In the final phase of the triggering movement which then follows, the triggering element 28 presses the blocking member 24 out of the blocking engagement with the blocking member 34.

As soon as the rotational block formed by the blocking members 24 and 34 is released, the rotational drive movement of the coupler input member 6' is initiated due to the drive force of the drive member 25 and is transferred onto the coupler output member 9 via the coupler engagement. Because it is guided—such that it is secured against rotating—in the linear guide 4a, the piston rod 15 is moved, in the threaded engagement with the coupler output member 9, in the advancing direction V, and product is delivered. This delivery movement is terminated by the stopping member 27 abutting the stopper of the thread of the blocking member 24 determining the zero dosage.

FIG. 1B shows the injection apparatus when a zero dosage is set, in the coupled state after the rotational block has been released, i.e. after the triggering element 28 has completely performed the triggering movement. If, advantageously, pressure is continuously exerted on the triggering element, the triggering sequence described above progresses automatically, from injecting to completely delivering the dosage set; for injecting, the casing is pressed against the surface of the skin.

FIG. 1C shows the injection apparatus after the reservoir 2 has been emptied. The casing part 1 has already been removed from the casing part 4. The piston rod 15 assumes its most distal position. The decoupling member 11' blocks the coupler input member 6' in the position retracted from the coupler intermediate member 7'. The functionality of the decoupling member 11' corresponds to that in other embodiments. Unlike the two first embodiments, however, the casing part 1 and the decoupling member 11' are not directly in a guiding engagement with each other, but rather via an adaptor structure 40. The adaptor structure 40 is a sleeve which is fixed in the casing part 4 in and counter to the direction of the coupler movement X in the connecting portion, but can be rotated about the central longitudinal axis of the casing part 4. The adaptor structure 40 forms a guiding curve 40a either as a cavity on or a breach in its shell area facing the decoupling member 11'. The guiding curve 40a exhibits the course of a threaded portion. The length measured over the circumference and the pitch of the guiding curve 40a measured with respect to the central longitudinal axis of the casing part 4 are dimensioned such that the decoupling member 11' is moved into the decoupling position shown in FIG. 1B by a quarter to a half revolution of the adaptor structure 40 relative to the decoupling member 11'. The movement of the decoupling member 11' exhibits an axial length which corresponds to the length X of the complete coupler movement. For generating the axial movement, the decoupling member 11' engages via its engaging element 12 with the guiding curve 40a. In this respect, reference is made to the statements regarding the first described exemplary embodiment.

When connecting the casing parts 1 and 4, the adaptor structure 40 forms a linear guide for the casing part 1. The casing part 1 is inserted into the adaptor structure 40, wherein a slight frictional lock and correspondingly a sliding guide for the casing part 1 exists. The casing part 1 cannot be rotated about the central longitudinal axis of the casing part 4 relative to the adaptor structure 40. The engagement, which accordingly is rotationally secured, is established right at the beginning of inserting the casing part 1 into the adaptor structure 40. Once the casing part 1 has been inserted until it abuts against the casing part 4, i.e., once the coupler is accommodated at 4a, the casing part 1 is rotated relative to the casing part 4 and slaves the adaptor structure 40 during this rotational movement, until the engaging element 12 of the decoupling member 11' abuts the end of the guiding curve 40a. In some embodiments, the rotational movement of the casing part 1 is preferably not possible until its axial abutting position, for which purpose a rotational block acting up until the abutting position can also be formed between the casing parts 1 and 4.

FIG. 2, as also FIG. 3, shows a cross-section of a life timer 100 which is integrated in the triggering element or dosing button 28 and connected to the threaded rod or piston rod 15 by means of a connecting piece 101. If the ampoule inserted into the injection device is full, then the switch 102 of the life timer can be activated via the piston rod 15 and the connecting piece 101, such that the LED 103a is briefly illuminated green. A chip 104 is provided on the circuit board 105a for evaluating the signals generated by the contact switch 102 and for controlling the LED 103a. The power necessary is provided by a battery 106 which is fastened to the circuit board 105a by means of a contact bow 107, wherein the life timer consisting of the components 102 to 107 is mounted in the receptacle 108. The elements of the one embodiment of the life timer, shown in cross-section in FIG. 2, are shown individually in FIG. 3. A time detection unit is integrated in the chip 104 and is started by the switch 102 by a signal, once an operating process has been detected for the first time. Once the maximum service life, for example, three years, stored in the chip has elapsed, the LED 103a is controlled such that it is illuminated red or blinks in order to signal to the user that he/she should no longer use the injection device and has to replace it. Additionally or alternatively, the number of ampoule changes, which can also be detected using the switch 102, can also be adduced in order to determine the end of the service life.

FIG. 4 shows an electronics sub-assembly integrated into the injection device, comprising an LCD display 110 which is illuminated from the rear side with green light by an LED 103b when the injection pen is operated within the service life, and with red light when the injection pen is operated outside a service life which may be defined or is ascertained in accordance with its operation. A spur wheel or toothed ring 111 meshes with a toothing of the coupler sleeve or coupler input member 6, 6' and transfers a rotational movement of the coupler input member 6, 6' to the encoder 112a, wherein the signal generated by the encoder 112a is processed by electronics and outputted for display on the LCD 110 to be read by the user. Since the coupler sleeve or coupler input member 6, 6' is moved as well during the setting process and during a delivery process, the encoder 112a coupled to the coupler sleeve 6 via the spur wheel 111 can always detect what dosage is still provided for dispensing from the injection device, such that the display on the LCD 110 regresses during the delivery process.

Aside from the coupler sleeve, a sensor or encoder can also be directly or indirectly coupled or connected to other elements of the pen provided for setting the dosage or for the delivery movement, such as a counting ring, the blocking member 24 or the connecting part 33.

Figure 5A:
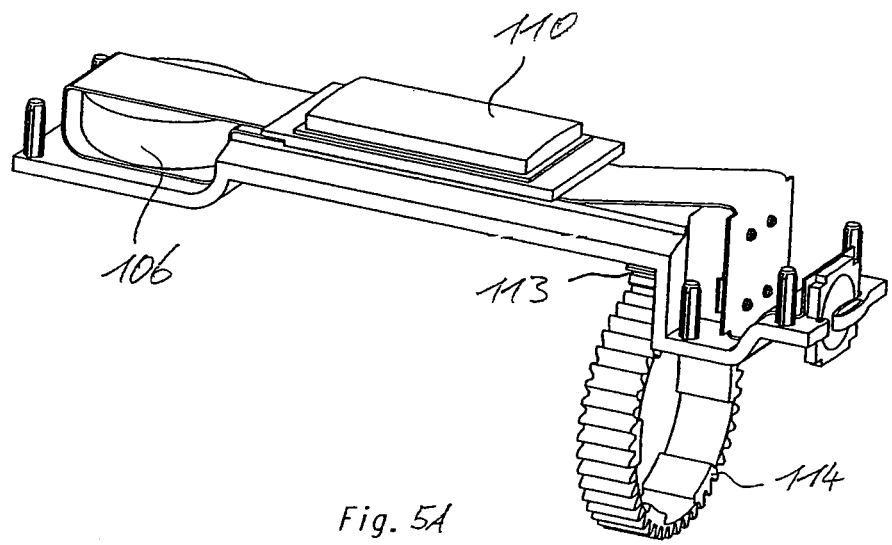
FIGS. 5A to 5C, depicts an embodiment of an electronic real-time display, comprising an encoder offset with respect to a dosing member, as a sensor.
Figure 5B:
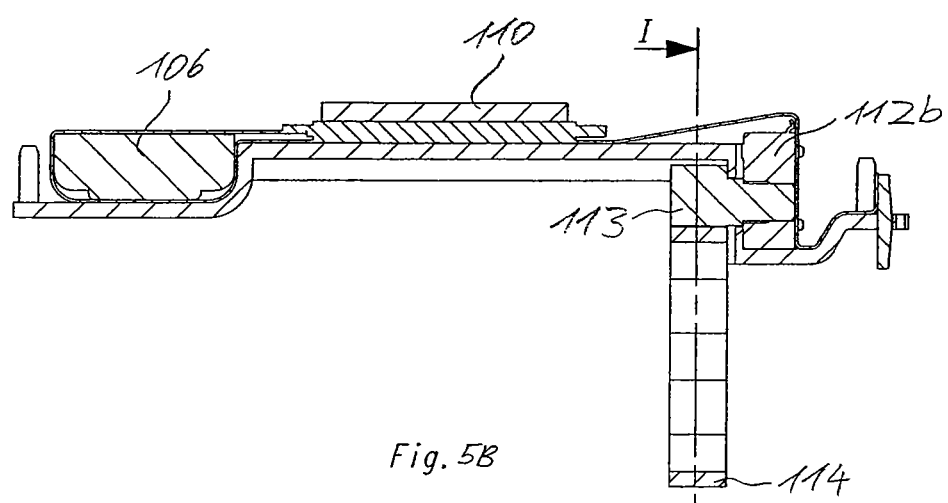
Figure 5C:
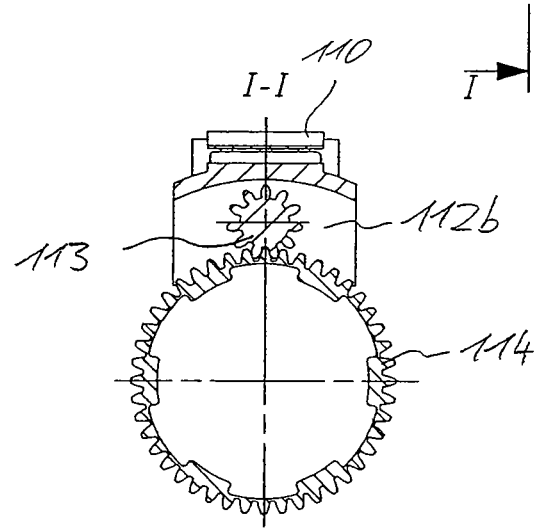

FIG. 5A shows a perspective view of another embodiment of an electronic real-time display, which is shown in cross-section in FIG. 5B and in a top view in FIG. 5C, wherein a toothed ring 114 is provided, such that it is secured against rotating, on a setting or dosing member of the injection device (not shown), and a toothed wheel 113 coupled to an encoder or rotational coder 112b having no stopper engages with said toothed ring 114 in order to detect a rotational movement of the dosing member and to display a dosage corresponding to the rotational movement on the LCD display 110. The encoder 112b could also be coupled to the coupler input member by means of a toothed wheel, as shown in FIG. 4.

FIG. 6 shows an embodiment of a mechanical coaxial real-time display, comprising a units counting ring 23a and a tens counting ring 23b as briefly described above. In the embodiment shown, the drive disc 120 connected to the coupler sleeve 6, 6' (not shown in FIG. 6) comprises three bearings 120a for planetary toothed wheels 121 which are driven by the drive disc 120. The planets 121 drive the units counting ring 23a which comprises an outer toothing 23c serving as a sun wheel which is coaxially offset and has a smaller diameter than the units counting ring 23a. On a hollow wheel 122, a bearing is provided for a coupling toothed wheel 123 which after each full revolution of the units counting ring 23a engages with the inner toothing 23d provided only on a partial region of the units counting ring 23a, in order to rotate the tens counting ring 23b further by 36 degrees. The hollow wheel 122 serves as a bearer for the unit shown in FIG. 6 and is held in the casing of the injection device. The rotational direction of the units counting ring 23a and the tens counting ring 23b corresponds to the rotational direction of the drive disc 120 coupled or connected to the coupler sleeve, such that a mechanical real-time display can be realised which continuously counts during the setting process, possible corrections to the setting and during the delivery process, and display the amount of the dosage still available for delivery after setting, in real-time.

FIG. 7 shows an embodiment in which the concept described with reference to FIG. 4 is realised not by an electronic display, but by a mechanical display, wherein the coupler sleeve is guided by a circuit board 105b and comprises teeth, texture or a toothing on its outer surface, with which the spur wheel 111 engages, as described with reference to FIG. 4. The outer toothing of the coupler sleeve is coupled to a toothed wheel formed as a slaving means 130 which transfers the rotational movement of the coupler sleeve onto an inner toothing 23e of the units counting ring 23a, wherein the units counting ring 23a is coupled to the tens counting ring 23b by means of the inner toothing 23d provided only over a part of the inner circumference, as described with reference to FIG. 6, in order to realise a real-time display. The units and tens counting rings 23a and 23b are transparent, such that a red or green light emitted by the LED 103, for indicating whether the injection device can still be used (green) or the service life has elapsed (red), can be perceived by a user reading the setting on the counting rings 23a, 23b.

FIG. 8 shows a cross-section of the device shown in FIG. 7, when assembled, wherein a section along the line indicated by III-III is shown in FIG. 9 and along the line indicated by IV-Iv in FIG. 10. The detail X in FIG. 9 is shown in FIG. 11.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A method for determining the end of a service life of an injection device has been reached, said injection device being capable of expelling the contents of more than one ampoule and having operating processes controlled by a controller, comprising the steps of:

providing a service life of the injection device, the service life having a beginning based on at least one of the operating processes of the injection device and an end;

establishing the beginning of the service life by using one or more sensors for detecting when the injection device is set or changed;

generating a signal which signals the end of the service life of the injection device; and providing an output device associated with the injection device that outputs at least one of an optical, acoustic or tactile signal which indicates to a user that the service life of the injection device is at the end.

2. The method according to claim 1, wherein the optical, acoustic or tactile signal is outputted continuously one of after the end of the service life or for a predetermined time period after detecting an operating process.

3. The method according to claim 2, wherein an operational process of the injection device is detected and used to calculate the beginning and end of the service life.

4. The method according to claim 3, wherein the operational process on which the end of the service life is based comprises the number of injection processes performed.

5. The method according to claim 1, further comprising software for the controller.

* * * * *